United States Patent [19]

Draper

[11] 4,267,173

[45] May 12, 1981

[54] USE OF 6β-FLUORO-7α-HALOGENOCORTICOIDS AS TOPICAL ANTI-INFLAMMATORIES AND PHARMACEUTICAL FORMULATIONS USEFUL THEREFOR

[75] Inventor: Richard W. Draper, North Caldwell, N.J.

[73] Assignee: Schering Corporation, Kenilworth, N.J.

[21] Appl. No.: 91,612

[22] Filed: Nov. 5, 1979

[51] Int. Cl.$^3$ .............................................. A61K 31/58
[52] U.S. Cl. ........................... 424/243; 260/239.55 D; 260/397.45
[58] Field of Search ..................... 424/243; 260/397.45

[56] References Cited

U.S. PATENT DOCUMENTS

| | | | |
|---|---|---|---|
| 3,148,184 | 9/1964 | Gould et al. | 260/239.55 |
| 3,173,914 | 3/1965 | Bowers | 260/239.55 |
| 3,264,332 | 8/1966 | Gould et al. | 260/239.55 |
| 3,496,273 | 2/1970 | Laurent et al. | 424/241 |
| 3,637,668 | 1/1972 | Laurent et al. | 260/239.5 |

*Primary Examiner*—Elbert L. Roberts
*Attorney, Agent, or Firm*—Mary S. King

[57] ABSTRACT

Described is the use of 6β-fluoro-7α-halogeno-1,4-pregnadiene-17α,21-diol-3,20-diones and their esters as topical anti-inflammatory agents, and pharmaceutical formulations thereof useful therefor. Preferred compounds are 6β,9α-difluoro-7α-chloro (or bromo)-16β-methyl-1,4-pregnadiene-11β,17α,21-triol-3,20-dione 17-mono- and 17,21-di-lower alkanoates.

17 Claims, No Drawings

USE OF 6β-FLUORO-7α-HALOGENOCORTICOIDS AS TOPICAL ANTI-INFLAMMATORIES AND PHARMACEUTICAL FORMULATIONS USEFUL THEREFOR

FIELD OF INVENTION

This invention relates to 6β-fluoro-7α-halogenocorticoids, pharmaceutical formulations thereof, and to the method of using these formulations in the treatment and control in inflammatory conditions.

More specifically, this invention relates to 6β-fluoro-7α-halogeno-1,4-pregnadiene-17α,21-diol-3,20-diones, pharmaceutical formulations thereof, and their use in the treatment and control of inflammatory conditions.

In particular, this invention relates to 6β-fluoro-7α,9α-dihalogeno-16-substituted-1,4-pregnadiene-17α,21-diol-3,20-dione 17-mono and 17,21-dilower alkanoates, particularly 16-methyl derivatives thereof, to topical pharmaceutical formulations thereof, and their use in the topcial treatment and control of anti-inflammatory conditions.

DESCRIPTION OF PRIOR ART

Described in the art are 6,7-dihalogenocorticoids and their use as intermediates.

U.S. Pat. Nos. 3,264,332 and 3,148,184 generically disclose 6,7-dihalogeno-3,20-dioxo-17α,21-dihydroxy-4-pregnenes and 1,4-pregnadienes having a hydrogen or halogen at C-9, a keto or β-hydroxyl at C-11 and a hydrogen or loweralkyl at C-16. The utility disclosed for these 6,7-dihalogenocorticoids are as intermediates in the preparation of the corresponding 6-halogeno-6-dehydro-7-unsubstituted corticoids, valuable as an antiinflammatory agents in the treatment of arthritis. U.S. Pat. No. 3,264,332 claims the process which utilizes the described 6,7-dihalogenocorticoids as intermediates and U.S. Pat. No. 3,148,184 claims the 6,7-dihalogenocorticoids per se. U.S. Pat. No. 3,264,332 discloses 6,7-dibromoprednisolone 21-acetate, 6,7-dibromoprednisone 21-acetate and the 9α-fluoro derivatives thereof and their conversion to the corresponding 6-bromo-6-dehydro-7-unsubstituted corticoid and U.S. Pat. No. 3,148,184 describes 6-fluoro-7-bromocortisone 21-acetate and its conversion to 6-fluoro-6-dehydrocortisone 21-acetate. However, neither of U.S. Pat. Nos. 3,264,332 or 3,148,184 specifically discloses a 6-fluoro-7-halogeno-1,4-pregnadiene of the instant invention.

U.S. Pat. No. 3,173,914 also discloses 6β-fluoro-7α-halogeno (other than fluorine)-4-pregnenes useful as intermediates in the preparation of the therapeutically valuable corresponding 6-fluoro-6-dehydro-7-unsubstituted corticoids. Specifically described in this patent are the following 1,2-dihydro analogs of the compounds of this invention: 6β-fluoro-7α-bromocortisone 21-acetate, 6β,9α-difluoro-7α-bromo-16α-hydroxy hydrocortisone 16,17-acetonide 21-propionate, and 6β,9α-difluoro-7α-bromo-16α-methylhydrocortisone and their conversion to the corresponding 6-fluoro-6-dehydro-7-unsubstituted-4-pregnenes.

Similarly, A. Bowers et al in J. Am. Chem. Soc. 82, 4001–4007 (1960) describe 6β-fluoro-7α-bromo-4-pregnene-17α,21-diol-3,20-dione 17,21-diacetate and its conversion to 4,6-pregnadiene-17α,21-diol-3,20-dione diacetate.

By my invention, I have made 6β-fluoro-7α-halogeno-1,4-pregnadienes, including 6β,7α-difluoro-pregnadienes, all of which heretofore have not been specifically described in the art. I have also discovered that these 6β-fluoro-7α-halogeno-1,4-pregnadienes exhibit high topical anti-inflammatory activity and are valuable in the treatment of inflammatory conditions in a warm blooded animal responsive to treatment with anti-inflammatory agents, when applied topically to the inflamed area. This is surprising since, heretofore the prior art has taught that 6,7-dihalogenocorticoids, including 6β-fluoro-7α-halogenocorticoids, are useful only as intermediates in the preparation of other therapeutically valuable corticoid derivatives.

DETAILED DESCRIPTION OF THE INVENTION

This invention resides in the concept of a 6β-fluoro-7α-halogeno-1,4-pregnadiene-17α,21-diol-3,20-dione having antiinflammatory activity, particularly 6β-fluoro-7α,9α-dihalogeno-16-substituted-1,4-pregnadiene-17α,21-diol-3,20-diones and their 17-monoalkanoate and 17,21-dilower alkanoate esters, useful as topical anti-inflammatory agents.

Specifically, the present invention relates to the method of treating an inflammatory condition in a warm-blooded animal responsive to treatment with anti-inflammatory agents, which comprises applying topically to the inflamed area, a nontoxic, anti-inflammatory effective amount of a 6β-fluoro-7α-dihalogeno-1,4-pregnadiene of the following formula I together with a non-toxic, pharmaceutically acceptable carrier:

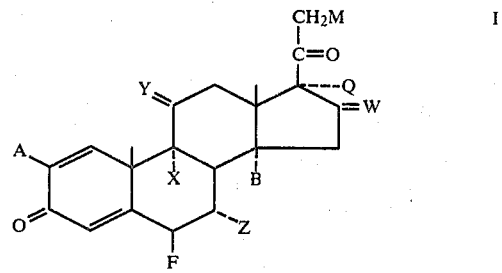

wherein

A is hydrogen, or when Y is (H, βOH), then A is also chlorine, bromine or methyl;

B is hydrogen, or taken together with Q is 14α,17α-alkylidenedioxy;

X is a member selected from the group consisting of hydrogen, fluorine, and chlorine;

Y is (H, β-OH), (H,β-OCOH), or when X is chlorine then Y is also (H,β-fluorine) or (H,β-chlorine);

Z is halogen;

Q is OV wherein V is hydrogen or an acyl radical of a hydrocarboncarboxylic acid having up to 8 carbon atoms;

W is a member selected from the group consisting of (H,H), (H, lower alkyl); (H, α–OV$_1$) wherein V$_1$ is hydrogen or an acyl radical of an acid selected from the group consisting of a hydrocarboncarboxylic acid having up to 12 carbon atoms and retinoic acid; =CHT wherein T is a member selected from the group consisting of hydrogen, lower alkyl, fluorine and chlorine; and W together with Q is 16α,17α-lower alkylidenedioxy, 16α,17α-cycloalkylidenedioxy or 16α,17α-alkylorthoalkanoate; and M is a member selected from the group consisting of chlorine and fluorine provided Q is other than hydroxy, and $OV_2$ wherein $V_2$ is hydrogen or an acyl radical of an acid selected from the group consisting of a hydrocarboncarboxylic acid having up to 12 carbon atoms, a hydrocarbonsulfonic acid having up to 12 carbon atoms, retinoic acid, and phosphoric acid and mono and di-alkali and alkaline earth metal salts thereof; and $OV_2$ together with OV is a member selected from the group consisting of alkylidenedioxy and alkylorthoalkanoate.

Alkyl groups within the definition of W and T are preferably lower alkyl, particularly those having up to four carbon atoms such as methyl, ethyl, n-propyl, isopropyl, n-butyl, sec.-butyl and tert.-butyl, although higher homologs such as pentyl and hexyl fall within the scope of this invention.

As used in the specification and claims of this application, the term "acyl" denotes a radical derived from an acid by removal of a hydroxyl group, e.g., acetyl is the acyl radical of acetic acid; benzoyl is the acyl radical of benzoic acid; and benzenesulfonyl is the acyl radical of benzenesulfonic acid.

The acyl radicals of the compounds of this invention as defined by V, $V_1$ and $V_2$ in formula I hereinabove include those derived from hydrocarboncarboxylic acids (V having up to 8 carbon atoms, $V_1$ and $V_2$ having up to 12 carbon atoms) which may be saturated, unsaturated, straight chain or branched chain, aliphatic, cyclic, cyclic-aliphatic, aromatic, aryl-aliphatic, or alkyl-aromatic, which may be substituted by hydroxy, alkoxy containing from 1 to 5 carbon atoms or by a halogen. Typical ester groups of the 6β-fluoro-7α-halogeno-16-substituted-1,4-pregnadiene-17α,21-diol-3,20-diones of this invention encompassed within the definition of V, $V_1$, and $V_2$ are thus derived from hydrocarboncarboxylic acids such as alkanoic acids exemplified by formic, acetic, propionic, trimethylacetic, butyric, isobutyric, valeric, isovaleric, caproic, tert.-butylacetic, enanthic, caprylic, capric, cyclopentylpropionic, undecylic, lauric, and adamantanecarboxylic acids, substituted alkanoic acids such as phenoxyacetic, trifluoroacetic, and β-chloropropionic acids; aromatic and substituted aromatic and heteroaromatic acids including benzoic, toluic, p-chlorobenzoic, p-fluorobenzoic, p-methoxybenzoic, 3',5'-dimethylbenzoic and isonicotinic acids; aryl-alkanoic acids such as phenylacetic, phenylpropionic, and β-benzoylaminoisobutyric acids; unsaturated acids such as acrylic and sorbic acids; hydrocarbonsulfonic acids such as methanesulfonic and p-toluenesulfonic acids; and dibasic acids such as succinic, tartaric, phthalic and benzene disulfonic acids and the alkali metal salts thereof.

The term "lower alkanoyloxy" is contemplated as including acid radicals of lower alkanoic acids having preferably up to 8 carbon atoms such as radicals obtained from acetic, propionic, butyric, valeric, caprylic, caproic, tert-butylacetic acid and the like.

The halogens at C-9 as defined by X in above formula I are chlorine and preferably fluorine. The halogens at C-7 as defined by Z in above formula I are fluorine, iodine, and preferably chlorine and bromine.

The alkylidene groups contemplated in the compounds of this invention are preferably lower alkylidenes, i.e., hydro-carbon radicals having preferably up to four carbon atoms including radicals such as methylene, ethylidene, n-propylidene, isopropylidene, n-butylidene, and sec.-butylidene and the like. The 16-lower alkylidene derivatives of this invention (i.e., when W in above formula I is =CHT) are double bonded to the D ring at C-16. The 16α,17α-alkylidenedioxy derivatives have the alkylidene terminal bonds attached to different oxygen atoms, i.e., to the oxygens at C-16 and C-17 in the case of 16α,17α-alkylidenedioxy derivatives, to oxygens at C-17 and C-21 in the case of the 17α,21-alkylidenedioxy derivatives, and to oxygens at C-14 and C-17 in the case of the 14α,17α-alkylidenedioxy derivatives.

The physical embodiments of the 6β-fluoro-7α-halogeno-16-substituted-1,4-pregnadiene-3,20-diones of formula I are characterized by being crystalline solids, usually white to off-white in color, which are insoluble in water (with the exception of alkali metal salts of esters such as the hemisuccinate and phosphate esters thereof) and soluble in most organic solvents, particularly in acetone, dioxane, dimethylformamide, and dimethylsulfoxide, although of limited solubility in nonpolar solvents such as dialkyl ethers and alkyl hydrocarbons.

The 6β-fluoro-7α-halogeno-16-substituted-1,4-pregnadiene-3,20-diones of formula I possess glucocorticoid activity and are particularly valuable as topical anti-inflammatory agents. Of the foregoing, preferred as topical anti-inflammatory agents are compounds having an acyloxy function at C-17 particularly those also having a C-16 -substituent and a halogen at C-9. Of these, particularly valuable are compounds having an alkyl group at C-16, particularly those unsubstituted at C-2 and C-14 and having an 11β-hydroxyl and 21-acyloxy function. Of these, preferred are the 7α-chloro- and 7α-bromo derivatives.

Particularly valuable topical anti-inflammatories of our invention are 6β-fluoro-7α-halogeno-16-methyl-1,4-pregnadiene-3,20-diones of following formula II:

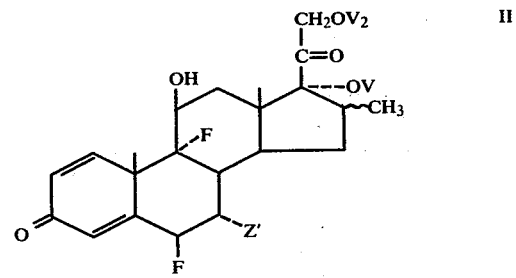

wherein
Z' is chlorine or bromine;
V and $V_2$ are independently hydrogen or an acyl radical of a hydrocarboncarboxylic acid having up to 4 carbon atoms.

The compounds of formula II wherein V alone or both V and $V_2$ are hydroxyl groups are valuable also as intermediates in preparing the preferred 17-mono- and 17,21-diester derivatives.

Of the compounds of formula II, particularly useful topical anti-inflammatory agents are those wherein V is an acyl radical of a hydrocarboncarboxylic acid having up to 4 carbon atoms, particularly the 17-propionate, 17-n-butyrate, and 17-isobutyrate derivatives which exhibit high topical anti-inflammatory activity with a minimum of systemic corticoid effects. The 16β-methyl-17-mono- and 17,21-diacyl derivatives of formula II are most valuable, particularly those having a 17-propionate ester.

The superior topical activity of the preferred 6β-fluoro-7α-halogeno-1,4-pregnadiene-3,20-diones of formula II, particularly of the 16β-methyl derivatives, are demonstrated by pharmacological tests in animals. Thus, for example, when tested in mice by a modification of the croton oil induced ear edema test (G. Tonelli et al, Endocrinology 77:625–634 (1965)), 6β,9α-difluoro-7α-bromo-16β-methyl-1,4-pregnadiene-11β,17α,21-triol-3,20-dione 17-propionate and 6β,9α-difluoro-7α-chloro-16β-methyl-1,4-pregnadiene-11β,17α,21-triol-3,20-dione 17,21-dipropionate exhibit topical activity about 1.1 times that of betamethasone 17-valerate (i.e., 9α-fluoro-16β-methyl-1,4-pregnadiene-11β,17α,21-triol-3,20-dione 17-valerate).

In similar manner, when tested by the above described tests in animals, other 6β-fluoro-7α-halogeno-1,4-pregnadiene-3,20-diones of formula II, e.g., the 17-propionate 21-acetate and 17-propionate 21-n-butyrate ester derivatives of 6β,9α-difluoro-7α-chloro-16β-methyl-1,4-pregnadiene-11β,17α,21-triol-3,20-dione and of the corresponding 7α-bromo derivatives, and 6β,9α-difluoro-7α-bromo-16β-methyl-1,4-pregnadiene-11β,17α,21-triol-3,20-dione 17,21-dipropionate exhibit high topical anti-inflammatory activity following topical application.

In addition to the foregoing preferred compounds, other useful 17-lower alkanoyloxy topical anti-inflammatory compounds of formula II include:

the 17-acetate, 17-propionate, 17-iso-butyrate, and 17-acetate 21-propionate of 6β,9α-difluoro-7α-chloro-16β-methyl-1,4-pregnadiene-11β,17α,21-triol-3,20-dione;

and the 17-acetate, 17-propionate, 17-iso-butyrate and the 17,21-diacetate of 6β,9α-difluoro-7α-bromo-16α-methyl-1,4-pregnadiene-11β,17α,21-triol-3,20-dione.

Other compounds of formula II include 17-hydroxy compounds such as

6β,9α-difluoro-7α-chloro-16β-methyl-1,4-pregnadiene-11β,17α,21-triol-3,20-dione 21-acetate, and 6β,9α-difluoro-7α-bromo-16α-methyl-1,4-pregnadiene-11β,17α,21-triol-3,20-dione 21-acetate and 21-trimethylacetate.

In addition to the preferred compounds of formula II, my invention includes the use as topical anti-inflammatories of other compounds of formula I including 7α-iodo compounds such as:

6β,9α-difluoro-7α-iodo-16β-methyl-1,4-pregnadiene-11β,17α,21-triol-3,20-dione 21-acetate, and 6β,9α-difluoro-7α-iodo-16α-methyl-1,4-pregnadiene-11β,17α,21-triol-3,20-dione and the 21-acetate thereof;

7α-fluoro compounds such as

6α,7α,9α-trifluoro-16β-methyl-1,4-pregnadiene-11β,17α,21-triol-3,20-dione 21-acetate and 17,21-dipropionate;

9α,11β-dihalogeno compounds such as

6β-fluoro-7α,9α,11β-trichloro-16α-methyl-1,4-pregnadiene-17α,21-diol-3,20-dione 21-acetate and 17,21-di-n-butyrate, and 16α-hydroxy pregnadienes (i.e., compounds of formula I) wherein W is (H,α—OH) and derivatives thereof such as 6β,9α-difluoro-7α-chloro-1,4-pregnadiene-11β,16α,17α,21-tetrol-3,20-dione and the 17-propionate, the 16,21-diacetate 17-propionate, the 17-benzoate, the 17-benzoate 21-acetate, and the 16α,17α-methylorthobenzoate 21-acetate esters thereof, the 16α,17α-isopropylidendioxy 21-acetate derivative thereof, and the corresponding 7α-bromo derivatives.

In general, the 6β-fluoro-7α-halogeno-3,20-dioxo-1,4-pregnadienes of formula I having hydroxyl groups or esters thereof at C-17 and C-21, particularly the 17α-hydrocarboncarboxylates thereof, and more particularly, the preferred compounds of formula II, are valuable anti-inflammatory agents when administered topically or locally, since they exhibit high antiinflammatory action. The compounds have the desirable high antiinflammatory action on topical administration with little risk of disturbance of the mineral balance.

The 6β-fluoro-7α-halogeno-3,20-dioxo-17α,21-dihydroxy-1,4-pregnadienes and the 17- or 21-esters or the 17,21-diesters thereof may be applied topically or locally in any of the conventional pharmaceutical forms. For example, they may be administered intra-articularly for long-term local activity with minimal systemic effects in aqueous suspensions as the 17,21-dihydrocarboncarboxylate esters e.g., the 17,21-dipropionate, 17,21-di-n-butyrate, and 17-propionate 21-acetate; or topically in creams, lotions, aerosols or ointments as the 17-mono-lower alkanoate or benzoate or the 17,21-diesters (e.g., 17,21-dipropionate) in the treatment of all corticosteroid responsive dermatoses such as contact, allergic, atopic, or seborrheic dermatitis, psoriasis and mange (in domesticated animals), or in the form of ophthalmic suspensions or nasal sprays. Advantageously, when topically administering preferred compounds of our invention, i.e., 7α-chloro and 7α-bromo-3,20-dioxo-1,4-pregnadienes of formula II, and particularly the 17-alkanoate and 17,21-dialkanoates thereof, the therapeutic topical dosages will generally be lower than those required when administering the corresponding 6,7-diunsubstituted analog. Thus, a preferred mode of the method-of-use aspect of our invention comprises the method of topically treating an inflammatory condition, e.g., inflammation of the skin or mucous membrane, which comprises topically applying to the affected area in a concentration effective for the topical treatment of inflammation of a 6β-fluoro-7α-halogeno-3,20-dioxo-1,4-pregnadiene of formula II in association with a pharmaceutical carrier.

Included within the term "topically applying" are topical application on skin whereby our compounds of formula II are effective in the treatment and control of all corticosteroid-responsive dermatoses, e.g., psoriasis, and of corticosteroid-responsive conditions such as alopecia areta or alopecia totalis; inhalation aerosol application whereby our preferred compounds of formula II are effective in the treatment of, e.g., respiratory inflammatory disorders such as asthma and allergic rhinitis; and intra-articular injection application whereby our preferred compounds of formula II are effective in the treatment of local inflammatory disorders such as rheumatoid arthritis, tennis elbow, bursitis, peritendinitis, capsulitis and gout.

Particularly valuable compounds of formula II for the topical treatment of inflammatory disorders are the 16β-methyl-17α,21-dilower alkanoates such as 6β,9α-difluoro-7α-chloro- and 6β,9α-difluoro-7α-bromo- derivatives of the 16β-methyl-1,4-pregnadiene-11β,17α,21-triol-3,20-dione 17,21-dipropionate and 17-propionate 21-acetate or 17-propionate 21-n-butyrate and the 6β,9α-difluoro-7α-bromo derivative of 16β-methyl-1,4-pregnadiene-11β,17α,21-triol-3,20-dione 17-propionate, all of which exhibit high topical activity with low systemic effects following topical application, as well as low parenteral and oral activities.

Also within the scope of our invention are pharmaceutical compositions for use in the treatment of inflammation comprising an effective amount of our novel 6β,9α-difluoro-7α-halogeno-16-substituted-1,4-pregnadienes of formula I in association with a compatible, pharmaceutically acceptable carrier or coating. Of the foregoing, preferred are pharmaceutical compositions for topical administration comprising the 6β,9α-difluoro-7α-chloro and 6β,9α-difluoro-7α-bromo-3,20-dioxo-16β-methyl-1,4-pregnadienes of formula II of which the 17-monoesters and 17,21-diesters, particularly those having 3 or 4 carbon atoms, are of greatest value as topical anti-inflammatories.

The pharmaceutical dosage forms are prepared according to procedures well known in the art and may contain other active ingredients, e.g., neomycin sulfate in cream for topical use.

The active steroid may be formulated into a preparation suitable for topical administration in conventional manner with the aid of one or more carriers or excipients. Examples of types of preparation include ointments, lotions, creams, gels, sprays, powders, drops (e.g., ear drops and eye drops), suppositories, foams or retention enemas (e.g., for the treatment of rectal or colonic inflammations) and tablets or pellets (e.g., for the treatment of aphthous ulcers) and aerosols. Ointments, creams and gels may, for example, be formulated with an aqueous or oily base with the addition of suitable thickening and/or gelling agents. Such bases may thus, for example, include water, and/or propylene glycol, and/or an oil such as liquid paraffin or a vegetable oil such as peanut oil or castor oil. Thickening agents which may be used according to the nature of the base include soft paraffin, aluminum stearate, cetostearyl alcohol, polyethylene glycols, woolfat, hydrogenated lanolin, beeswax, etc.

Lotions may be formulated with an aqueous or oily base and will in general also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The pharmaceutical compositions according to the invention may also include one or more preservatives of bacteriostatic agents, e.g., methyl hydroxybenzoate, propyl hydroxybenzoate, chlorocresol, benzalkonium chlorides, etc.

The compositions according to the invention may also contain other active ingredients such as antimicrobial agents, particularly antibiotics.

The proportion of active steroid in the compositions according to the invention depends on the precise type of formulations to be prepared but will generally be within the range of from 0.0001% to 5% by weight. Generally, however, for most types of preparations advantageously the proportion used will be within the range of from 0.001 to 0.5% and preferably 0.01 to 0.25%.

The following formulations are to exemplify some of the topical dosage forms in which the anti-inflammatory agents of this invention may be employed. In each, the active ingredient is designated by the term "Drug" which is meant to indicate one of the following compounds:

6β,9α-difluoro-7α-bromo-16β-methyl-1,4-pregnadiene-11β,17α,21-triol-3,20-dione 17-propionate and
6β,9α-difluoro-7α-chloro-16β-methyl-1,4-pregnadiene-11β,17α,21-triol-3,20-dione 17,21-dipropionate. It is understood, however, that each of these compounds may be replaced by equally effective quantities of other compounds defined by formula I, particularly those of formula II.

FORMULATIONS

| Formulation 1 - Ointment | |
|---|---|
| | mg/g |
| Drug | 0.1–5.0 |
| Mineral Oil | 20.0 |
| White Petrolatum to make | 1.00 g |

Melt and heat the white petrolatum to 55° C. Heat the mineral oil to 40° C. Disperse the Drug in the mineral oil and mill the suspension. Add the suspension to the melted white petrolatum with agitation. Start cooling and continue to agitate until the temperature reaches 30° C.

| Formulation 2 - Glycol Ointment | |
|---|---|
| | mg/g |
| Drug | 0.1–0.5 |
| Hexylene Glycol | 100.0 |
| Propylene Glycol Monostearate | 20.0 |
| White Wax | 60.0 |
| White Petrolatum to make | 1.00 g |

Melt and heat together to 60°–65° C. the propylene glycol monostearate, white wax and white petrolatum. Heat the hexylene glycol to 40° C. and dissolve the Drug in it. Add the solution of the hexylene glycol to the above oily phase (cooled to 55° C.) with agitation. Start cooling and continue to agitate until the temperature reaches 30° C.

| Formulation 3 - Lotion | |
|---|---|
| | mg/g |
| Drug | 0.1–5.0 |
| Ethyl Alcohol | 400.0 |
| Polyethylene Glycol 400 | 300.0 |
| Hydroxypropyl Cellulose | 5.0 |
| Propylene Glycol to make | 1.0 g |

Dissolve the Drug in the mixture of ethyl alcohol polyethylene glycol and propylene glycol. Slowly add the hydroxypropyl cellulose and continue to agitate until the hydroxypropyl cellulose is completely dispersed and wetted and a clear lotion is produced.

| Formulation 4 - Gel | |
|---|---|
| | mg/g |
| Drug | 0.1–5.0 |
| Ethyl Alcohol | 400.0 |
| Polyethylene Glycol 400 | 300.0 |
| Carbopol 940 (Goodrich) | 15.0 |
| Potassium Hydroxide | 3.0 |
| Propylene Glycol to make | 1.00 g |

Dissolve the Drug in a mixture of the ethyl alcohol, polyethylene glycol 400 and a portion of the propylene glycol. Use the remaining portion of the propylene glycol to dissolve the potassium hydroxide. Add the Carbopol 940 slowly to the above mixture and continue to agitate until the Carbopol 940 is completely dispersed and wetted. Add slowly the potassium hydroxide solution and continue to agitate until a clear gel is produced.

| Formulation 5 - Cream | |
|---|---|
| | mg/g |
| Drug, Micronized | 0.1–5.0 |
| Isopropyl Palmitate | 100.0 |
| Glyceryl Stearate | 80.0 |
| Promulgen-Type D (Robinson, Wagner Co.) | 50.0 |
| White Wax | 50.0 |
| Propylene Glycol | 100.0 |
| Purified water to make | 1.00 g |

Melt together and heat to 75° C. the white wax, glyceryl stearate, Promulgen-Type D and a portion of the isopropyl palmitate and maintain the temperature. Disperse the Drug in the remaining portion of the isopropyl palmitate and mill the dispersion. While agitating add the dispersion to the above oily phase. Heat together the water and the propylene glycol to 75° C. Add the solution to the above oily phase with agitation. Start cooling and continue to agitate until the temperature reaches 30° C.

| Formulation 6 - Topical Aerosol | |
|---|---|
| | mg/can |
| Drug | 6.4 |
| Mineral Oil | 1,250.0 |
| Neobee M-5 (Caprylic/Capric Glyceride) (PVO International, Inc.) | 3,743.6 |
| Dichlorodifluoromethane | 17,200.0 |
| Trichloromonofluoromethane | 68,800.0 |
| | 91,000.0 |

Dissolve the Drug in Neobee M-5 (Caprylic/Capric Glyceride) and add mineral oil. Place this concentrate into an aerosol and crimp a valve on the can. Inject the dichlorodifluoromethane and trichloromonofluoromethane mixture into the container through the valve.

| Formulation 7 - Inhalation Aerosol | |
|---|---|
| | mg/can |
| Drug | 12.60 |
| Oleic Acid | 1.26 |
| Trichloromonofluoromethane | 5,686.14 |
| Dichlorodifluoromethane | 14,700.00 |
| | 20,400.00 |

Disperse the Drug in trichloromonofluoromethane containing oleic acid and meter the resulting suspension into the cans. Crimp a valve onto the can and inject dichlorodifluoromethane into the container through the valve.

| Formulation 8 - Intra-Articular Injection | |
|---|---|
| | mg/ml |
| Drug | 0.1–5.0 |
| Sodium Phosphate, dibasic, anhydrous R | 2.00 |
| Sodium Chloride, USP | 5.00 |
| Disodium EDTA, USP (Disodium Ethylenediamine tetraacetate) | 0.10 |
| Polysorbate 80, USP | 0.50 |
| Benzyl Alcohol, R | 9.00 |

| Formulation 8 - Intra-Articular Injection | |
|---|---|
| | mg/ml |
| Methylparaben, USP | 1.80 |
| Propylparaben, USP | 0.20 |
| Sodium CMC (Sodium Carboxymethylcellulose) | 5.00 |
| Polyethylene Glycol 4000, USP | 20.00 |
| HCl 1N qs pH 7.1 | |
| Distilled Water qs ad | 1.00 ml |

Method of Manufacture:

| Vehicle A (10X) | mg/ml | gm/5 liters |
|---|---|---|
| | | (required to make 50 liters final suspension) |
| Sodium Phospate, Dibasic, Anhydrous, R | 20.0 | 100.0 |
| Sodium Chloride, R | 50.0 | 250.0 |
| Disodium EDTA, Dihydrate, R | 1.0 | 5.0 |
| Polysorbate 80, USP | 5.0 | 25.0 |
| 1N HCl qs pH 7.10 | | |
| Water for injection qs ad | 1.0 ml | 5.0 liters |

1. Collect approximately 80% of water for injection of the final volume of Vehicle A. Sparge with nitrogen.
2. Dissolve with agitation the disodium EDTA, dibasic sodium phosphate, sodium chloride. Discontinue nitrogen sparging and disperse the Polysorbate 80 while overlaying with nitrogen.
3. Adjust the pH of the solution to 7.1 with 1.0 N hydrochloric acid solution, then add sufficient water to bring Vehicle A to the required volume. Sterile filter, overlay with sterile nitrogen.

| Vehicle B (1.33X) | mg/ml | gm/37.5 liters |
|---|---|---|
| | | (required to make 50 liters final suspension) |
| Benzyl Alcohol, R | 12.000 | 450.0 |
| Methylparaben, USP | 2.400 | 90.0 |
| Propylparaben, USP | 0.266 | 10.0 |
| Sodium Carboxymethylcellulose | 6.670 | 250.0 |
| Polyethylene Glycol 4000, USP | 26.670 | 1,000.0 |
| Water for injection qs ad | 1.000 ml | 37.5 liters |

1. Charge approximately 95% (35.6 liters) of the water for injection.
2. Separately dissolve the methyl and propylparaben in the benzyl alcohol, then add the sodium carboxymethylcellulose and add this slurry to the water for injection.
3. Charge the polyethylene glycol 4000, USP.
4. Bring the volume of Vehicle B to the final volume and pass through an 8.0μ Millipore membrane into containers for autoclaving.

| Final Suspension | per liter | per 50 liters |
|---|---|---|
| Drug | 0.1 to 5.0 gm | 5.0 to 250 gm |
| Vehicle A | 100.00 ml | 5,000.0 ml |
| Vehicle B | 750.00 ml | 37,500.0 ml |
| Water for injection qs ad | 1,000.00 ml | 50.0 liters |

1. In a suitable sterile area, charge 27.5 liters of Vehicle B to a compounding tank.
2. Disperse the Drug in a minimum quantity of Vehicle A, and pass the slurry through a colloid mill until the particles are well dispersed, then rinse the mill with the remainder of Vehicle A.

3. Add to the slurry an approximate equal volume of Vehicle B, pass the resultant flocculated suspension through the mill, then pass the suspension through a sterile mesh screen into the compounding tank.

4. Rinse the mill with part of Vehicle B followed by water, pass the rinse through the screen into the compounding tank. Add the remainder of Vehicle B, then water, to bring the batch up to the required volume. Mix well.

5. Fill aseptically into siliconed vials and/or ampules, overlay with nitrogen, and stopper.

| Formulation 9 - Solution | |
|---|---|
| | mg/ml |
| Drug | 0.1–5.0 |
| N-methylpyrrolidone | 200 |
| Isopropyl myristate | 50 |
| Isopropyl alcohol | qs to 1.0 ml |

Dissolve the Drug in a portion of the N-methylpyrrolidone. Mix the isopropyl myristate with a portion of isopropyl alcohol. Mix the two solutions, add the remainder of the N-methylpyrrolidone, then isopropyl alcohol to the desired volume.

| Formulation 10 - Gel | |
|---|---|
| | mg/g |
| Drug | 0.1–5.0 |
| Propylene Glycol | 250.0 |
| Ethyl Alcohol | 300.0 |
| Hydroxypropyl Methyl Cellulose | 25.0 |
| Citric Acid | 7.4 |
| Sodium Citrate | 6.4 |
| Purified Water | To make 1,000.0 |

Dissolve the Drug in a mixture of the ethyl alcohol and propylene glycol. Add hydroxypropyl methyl cellulose slowly to the above mixture and agitate until the hydroxypropyl methyl cellulose is completely dispersed. Dissolve citric acid and sodium citrate in water and add this solution to the above mixture. Continue to agitate until a clear gel is produced.

Method of Preparation of Compounds of the Invention

The 6$\beta$-fluoro-7$\alpha$-halogeno-1,4-pregnadienes of formulae I and II, while not specifically described in the art, are prepared by known reactions for the addition of halogens to a 6-dehydro bond in a 4,6-pregnadiene such as those described in U.S. Pat. Nos. 3,148,184 and 3,173,914 and by A. Bowers, et al. in J. Am. Chem. Soc. 82, 4001–4007 (1960).

In general, the 6$\beta$-fluoro-7$\alpha$-halogeno-1,4-pregnadiene-3,20-diones of this invention other than the 6$\beta$,7$\alpha$-difluoro derivatives are prepared from the corresponding 6,7-unsubstituted-1,4,6-pregnatriene by reaction under anhydrous conditions with hydrogen fluoride and an N-halogenated hydrocarbon amide or imide, in the presence of a non-reactive organic aprotic solvent such as ether, tetrahydrofuran, methylene chloride, chloroform, dioxane and, preferably, a mixture of sulfolane (i.e., tetramethylenesulfone) and pyridine. By "non-reactive" is meant any organic solvent which will not react with the steroid substrate or the hydrogen fluoride or N-halogenated amide or imide which would cause transformations resulting in competing side reactions.

Useful N-halogenated amide reagents for the foregoing process are N-chloroacetamide, N-bromoacetamide, 1,3-dibromo-5,5-dimethylhydantoin and 3-bromo-4,4-dimethyl-2-oxazolidinone. Preferred as reagents, however, are N-halogenated succinimides, i.e., N-chlorosuccinimide, N-bromosuccinimide and N-iodosuccinimide.

The process whereby is prepared a 6$\beta$-fluoro-7$\alpha$-chloro (or bromo- or iodo)-1,4-pregnadiene by reaction of a 1,4,6-pregnatriene with a positive halogeno species (liberated from an N-halo organic amide or imide, e.g., N-chlorosuccinimide), and followed by nucleophilic attack of fluoride ion in an anhydrous aprotic solvent, is preferably carried out at temperatures in the range of from about $-50°$ C. to about room temperature (e.g., $20°$ C.) although lower temperatures (e.g., $-60°$ C.) and temperatures as high as about $60°$ C. may be employed. The reaction time depends upon the N-halogenated organic amide or imide, the solvent, temperature, and concentration being employed. The usual reaction time is from 2 to 24 hours, although some may be completed in as little as 30 minutes or may require several days.

Substituents present in the 3,20-dioxo-1,4,6-pregnatriene starting steroids of this process usually remain unchanged under the conditions of the process. Indeed, it is usually preferable to have all the substituents desired in the 6$\beta$-fluoro-7$\alpha$-halogeno-3,20-dioxo-1,4-pregnadiene product present in the 3,20-dioxo-1,4,6-pregnatriene starting compound. Thus, by way of example, the 3,20-dioxo-1,4,6-pregnatriene starting steroids of this process may be substituted at C-2 by methyl or halogen, at C-11 by oxygen, hydroxy, and halogen; at C-16 by acyloxy, alkyl, alkylidene, halogenoalkylidene, hydroxy, and at C-17 there is present a corticoid side chain and derivatives thereof.

Generally, when carrying out this process, to a solution of a 1,4,6-pregnatriene-17$\alpha$,21-diol-3,20-dione (e.g., 9$\alpha$-fluoro-16$\beta$-methyl-1,4,6-pregnatriene-11$\beta$,17$\alpha$,21-triol-3,20-dione 21-acetate) in an aprotic solvent (preferably tetramethylenesulfone) there is added anhydrous hydrogen fluoride (preferably in pyridine) followed by an N-halogenoimide or amide (e.g., N-chlorosuccinimide) the quantity of hydrogen fluoride being in excess to that of steroid and the molar quantity of N-halogenosuccinimide being about 1.1 to 2 per mole of steroid. After the reaction is complete, as determined by thin layer chromatography, the reaction mixture is poured into aqueous sodium bicarbonate, and the resultant 6$\beta$-fluoro-7$\alpha$-halogeno-1,4-pregnadiene-17$\alpha$,21-diol-3,20-dione (e.g., 6$\beta$,9$\alpha$-difluoro-7$\alpha$ chloro-1,4-pregnadiene-11$\beta$,17$\alpha$,21-triol-3,20-dione 21-acetate) is isolated via filtration or extraction techniques and purified utilizing known techniques, usually via chromatography and/or crystallization.

The 3,20-dioxo-1,4,6-pregnatriene starting compounds of the foregoing process are either known compounds or are conveniently prepared from the corresponding 3,20-dioxo-1,4-pregnadiene utilizing techniques known to effect dehydrogenation between C-6 and C-7 such as those utilizing chloranil or 2,3-dichloro-5,6-dicyanobenzoquinone (DDQ) or by bromination at C-6 followed by dehydrobromination. Since ester groups are usually present in the starting steroid, anhydrous conditions are preferably employed to minimize the possibility of hydrolysis.

The 6$\beta$,7$\alpha$-difluoro compounds of our invention are conveniently prepared by reaction of the corresponding 1,4,6-pregnatriene-17$\alpha$,21-diol-3,20-dione (e.g., 9$\alpha$-fluoro-16$\beta$-methyl-1,4,6-pregnatriene-11$\beta$,17$\alpha$,21-triol- 3,20-dione 21-acetate) in an organic solvent (e.g., methylene chloride) with gaseous fluorine diluted with an inert gas (e.g., argon or nitrogen) at temperatures in the range of from about −100° C. to about 0° C., preferably at about −78° C. until the starting steroid is consumed as determined by thin layer chromatography. The reaction time ranges from about one to 10 hours, and usually is about two hours. The resulting 6β,7α-difluoro-1,4-pregnadiene-17α,21-diol-3,20-dione (e.g., 6β,7α,9α-trifluoro-16β-methyl-1,4-pregnadiene-11β,17α,21-triol-3,20-dione 21-acetate) is conveniently isolated by removal of the excess gaseous fluorine, then evaporation of the solvent and purification of the residue via known techniques, usually chromatography and crystallization.

Organic solvents useful in preparing the 6β,7α-difluoro compounds of this invention include lower alkanoic acids and halogenated derivatives thereof (e.g., acetic acid and trifluoroacetic acid); fluorinated and chlorinated lower alkanes (e.g., chloroform, freons, and methylenechloride); fluorinated lower alkanols (e.g. trifluoromethylmethanol); acetonitrile; dilower alkyl sulfones (e.g., dimethylsulfone); cyclic sulfones (e.g., sulfolane) as well as co-solvents such as dioxan and tetrahydrofuran which frequently improve the solubility of the starting 1,4,6-pregnatriene. Preferred solvents include the chlorinated hydrocarbons and/or freons together with tetrahydrofuran to improve solubility.

The gaseous mixtures of fluorine in an inert gas are preferably very dilute, the volume of fluorine to inert gas (e.g., nitrogen), being usually less than 10% (v/v) and optimally being about 2.5%.

The yields of 6β,7α-difluoro-1,4-pregnadienes are often improved by the presence of a free radical inhibitor (e.g., oxygen, nitrobenzene or benzoquinone) in the solvent or inert gas prior to addition of fluorine. Yields are also improved by the addition of a hydrogen fluoride scavenger such as sodium trifluoroacetate, alkali metal fluorides (e.g., potassium fluoride and sodium fluoride), siloxane, or an activated molecular sieve.

When preparing 9α,11β-dihalogeno derivatives of this invention, i.e., 6β-fluoro-7α,9α,11β-trihalogeno derivatives such as 6β-fluoro-7α,9α,11β-trichloro-16α-methyl-1,4-pregnadiene-17α,21-diol-3,20-dione 17,21-dipropionate, the 9α-halogeno and 11β-halogeno atoms may be present in the molecule prior to introduction of the 6β-fluoro-7α-halogeno groups. Alternatively, the 9α,11β-dihalogeno substituents may be introduced into a 6β-fluoro-7α-halogeno-3,20-dioxo-1,4,9(11)-pregnatriene derived from a 6β-fluoro-7α-halogeno-9α-unsubstituted-11β-hydroxy-3,20-dioxo-1,4-pregnadiene of this invention by reaction thereof with methanesulfonyl chloride and collidine in dimethylformamide in the presence of sulfur dioxide. For example, reaction of a 6β-fluoro-7α-halogeno-9(11)-dehydro derivative (e.g., 6β-fluoro-7α-chloro-16α-methyl-1,4,9(11)-pregnatriene-17α,21-diol-3,20-dione 17,21-dipropionate) with chlorine in a halogenated solvent (e.g., chloroform in the presence of a tertiary amine hydrochloride (e.g., pyridine hydrochloride) according to known procedures, yields the corresponding 6β-fluoro-7α,9α,11β-trichloro derivative (e.g., 6β-fluoro-7α,9α,11β-trichloro-16α-methyl-1,4-pregnadiene-17α,21-diol-3,20-dione 17,21-dipropionate). Additionally, reaction of the foregoing 6β-fluoro-7α-halogeno-9(11)-dehydro derivative with N-chlorosuccinimide and perchloric acid utilizing known techniques yields the corresponding 9,11-chlorohydrin, e.g., 6β-fluoro-7α,9α-dichloro-16α-methyl-1,4-pregnadiene-11β,17α,21-triol-3,20-dione 17,21-dipropionate. Similarly, reaction of a 6β-fluoro-7α-halogeno-9(11)-dehydro derivative (e.g., 6β-fluoro-7α-bromo-16α-methyl-1,4,9(11)-pregnatriene-17α,21-diol-3,20-dione 17-benzoate 21-propionate) with N-chlorosuccinimide and perchloric acid yields the corresponding 6β-fluoro-7α-halogeno-9α-chloro-11β-hydroxy compound of this invention, i.e., 6β-fluoro-7α-bromo-9α-chloro-16α-methyl-1,4-pregnadiene-11β,17α,21-triol-3,20-dione 17-benzoate 21-propionate.

The 16-methylene derivatives of formula I are conveniently derived from the corresponding 16β-methyl derivatives utilizing procedures well known in the art. For example, treatment of a 6β-fluoro-7α-halogeno-16β-methyl-1,4-pregnadiene of this invention (e.g., 6β,9α-difluoro-7α-chloro-16β-methyl-1,4-pregnadiene-11β,17α,21-triol-3,20-dione 21-acetate) with potassium acetate in dimethylformamide at elevated temperatures (e.g., 100° C.) yields the corresponding 16-methyl-16-dehydro derivative (e.g., 6β,9α-difluoro-7α-chloro-16-methyl-1,4,16-pregnatriene-11β,21-diol-3,20-dione 21-acetate) which, upon reaction with m-chloroperbenzoic acid in chloroform at room temperature, yields the corresponding 16α,17α-oxido derivative (e.g., 6β,9α-difluoro-7α-chloro-16α,17α-oxido-16β-methyl-1,4-pregnadiene-11β,21-diol-3,20-dione 21-acetate). Reaction of the foregoing 16β-methyl-16α,17α-oxido derivative with hydrogen chloride in acetic acid at room temperature then yield a 6β-fluoro-7α-halogeno-16-methylene-17α-hydroxy-1,4-pregnadiene of formula I (e.g., 6β,9α-difluoro-7α-chloro-16-methylene-1,4-pregnadiene-11β,17α,21-triol-3,20-dione 21-acetate).

The 16-fluoromethylene- and 16-chloromethylene derivatives of formula I can be derived from the corresponding 16-methylene derivatives via known methods. For example, reaction of a 6β-fluoro-7α-halogeno-16-methylene-1,4-pregnadiene of formula I (e.g., 6β,9α-difluoro-7α-chloro-16-methylene-1,4-pregnadiene-11β,17α,21-triol-3,20-dione 21-acetate) with perchloryl fluoride followed by hydrogen chloride in acetic acid at room temperature yields a 16-fluoromethylene of formula I (e.g., 6β,9α-difluoro-7α-chloro-16-fluoromethylene-1,4-pregnadiene-11β,17α,21-triol-3,20-dione 21-acetate). alternatively, reaction of the foregoing 16-methylene derivative with N-chlorosuccinimide followed by hydrogen chloride in acetic acid at room temperature yields the corresponding 16-chloromethylene derivative (e.g., 6β,9α-difluoro-7α-chioro-16-chloromethylene-1,4-pregnadiene-11β,17α,21-triol-3,20-dione 21-acetate).

The 17α-acyloxy-21-chloro-6β-fluoro-7α-halogeno-1,4-pregnadienes of formula I wherein W is (H,H), (H, alkyl) or (H,αOV₁) are conveniently prepared from the corresponding 16-substituted-17α,21-dihydroxy-1,4-pregnadiene 17α,21-orthoester by reaction with triphenylmethyl chloride or a triarylsilyl chloride or trialkylsilyl chloride according to procedures described in U.S. Pat. Nos. 3,992,422 and 4,021,459. Additionally, the 21-chloro- and 21-fluoro- derivatives of formula I wherein Q is other than hydroxy can be derived from the corresponding 21-methanesulfonate ester (e.g., 6β,9α-difluoro-7α-chloro-16β-methyl-1,4-pregnadiene-11β,17α,21-triol-3,20-dione 17-propionate 21-methanesulfonate) by reaction with lithium fluoride or lithium chloride in dimethylformamide in known manner to produce, respectively, the corresponding 21-fluoro derivative (e.g., 6β,9α,21-trifluoro-7α-chloro-16β-methyl-1,4-pregnadiene-11β,17α-diol-3,20-dione 17-propionate) and 21-chloro derivative (e.g., 6β,9α-difluoro-7α,21-dichloro-16β-methyl-1,4-pregnadiene-11β,17α-diol-3,20-dione 17-propionate).

HYDROLYSIS AND PREPARATION OF ESTER DERIVATIVES

6β-Fluoro-7α-halogeno-3,20-dioxo-1,4-pregnadienes having ester functions such as at C-16, C-17 and/or at C-21 can be converted in known manner into 6β-fluoro-7α-halogeno-3,20-dioxo-1,4-pregnadienes having free hydroxyl groups as, for example, by the action of mild basic saponification agents, preferably 10% aqueous sodium bicarbonate. By regulating the reaction time and quantity of reagent, a 17,21-dihydrocarboncarboxylate can be converted to the corresponding 17-monoester or to the corresponding 17,21-diol.

Another method of preparing a 6β-fluoro-7α-halogeno-3,20-dioxo-17,21-dihydroxypregnadiene is by coversion of the alkylidenedioxy functions at C-17(21) in known manner in an acidic medium (e.g., 50% aqueous acetic acid) under an atmosphere of nitrogen.

As disclosed hereinabove, the preferred compounds of our invention are those which are esterified at C-17, including 17-mono- and 17,21-diesters, the 17-propionate, 17-iso-butyrate, and, 17-n-butyrate being particularly preferred ester derivatives. Usually, it is advantageous to introduce the ester groups into the 3,20-dioxo-1,4,6-pregnatriene precursors prior to introduction of 6β-fluoro-7α-halogeno atoms.

The 17α,21-diesters are prepared according to known methods by acylation of the corresponding 17α,21-diols or 17α-hydroxy-21-acyloxy compounds, preferably by reaction of the steroid with a appropriate acid anhydride in the presence of a strong acid catalyst such as e.g., p-toluenesulfonic acid, perchloric acid or strongly acidic cation exchange resins, or by using trifluoroacetic anhydride with an appropriate lower alkanoic acid.

Prior to esterifying a 17α-hydroxyl group, any 11β-hydroxyl function ought be protected such as by preparing the 11β-trifluoroacetate ester which, after esterification at C-17, may be hydrolyzed with mild base (e.g., dilute aqueous sodium benzoate) without hydrolyzing the other ester groups at C-17 and/or at C-21. Alternatively, the esterification may be carried out on an 11-oxo intermediate which, after esterification at C-17 and C-21 and introduction of the halogens at C-6 and C-7 may be reduced with sodium borohydride to produce the corresponding 6β-fluoro-7α-halogeno-11β-hydroxy-17,21-diacyloxypregnadiene.

The 17,21-diesters may also be prepared by acylation of the corresponding 21-hydroxy-17α-monoesters by treatment thereof with the appropriate acid anhydride or acid chloride undr basic conditions, preferably in the presence of a tertiary organic base, e.g., pyridine, quinoline, N-methylpiperidine, N-methylmorpholine, p-dimethylaminopyridine or dimethylaniline.

The 17α-monoesters of our invention may be prepared by hydrolysis of a corresponding 17,21-orthoester or 17α,21-diester.

In preparing 17-monoesters via hydrolysis of a 17,21-orthoester, the 17,21-orthoester intermediate is conveniently prepared by reaction of the 17α,21-diol with an alkylorthoester followed by hydrolysis of the resulting 17,21-orthoester under mild conditions, i.e., hydrolysis in the presence of an acid catalyst (e.g., a lower alkanoic acid such as acetic or propionic) or a strong mineral acid such as hydrochloric, sulfuric acid. When no substituent is present at C-16 the hydrolysis is preferably carried out under buffered conditions at a pH in the range of 4 to 6.

To prepare 16α,17α- or 17α,21-alkylidenedioxy derivatives of the 1,4,6-pregnatriene precursors and the corresponding 6β-fluoro-7α-halogeno compounds of this invention, the corresponding 16α,17α-dihydroxy- or 17α,21-dihydroxy steroid intermediate is reacted with a ketone or aldehyde (e.g., acetone, acetaldehyde, acetophenone) in the presence of a mineral acid (e.g., hydrochloric acid) whereby is obtained the corresponding 16α,17α-alkylidenedioxy or 17α,21-alkylidenedioxy derivative.

The 21-dihydrogenphosphate esters of this invention are prepared by reaction of the corresponding 21-hydroxy compound with pyrophosphoryl chloride utilizing known techniques. Both the mono- and dialkali salts and alkaline earth metal salts of the dihydrogen phosphate ester thereby formed may be obtained by neutralizing said dihydrogen phosphate ester with an alkali methoxide or alkaline earth methoxide.

The processes described hereinabove are illustrated in detail in the Examples hereinbelow and should not be construed as limiting the invention, equivalents thereof and products produced thereby which will be obvious to one skilled in the art being considered a part of the invention.

The molecular structure of the compounds of the invention described in detail herein were assigned on the basis of their method of preparation and study of their chromatographic characteristics and of their nuclear magnetic resonance (nmr), mass spectra and ultraviolet spectra, and were confirmed by the correspondence between calculated and found values of elementary analyses for the elements.

EXAMPLE 1

6β-FLUORO-7α-CHLORO-16-METHYL-1,4-PREGNADIENE-17α,21-DIOL-3,20-DIONE 21-ACETATE DERIVATIVES

A.

6β,9α-Difluoro-7α-Chloro-16β-Methyl-1,4-Pregnadiene-11β,17α,21-Triol-3,20-Dione 21-Acetate To a solution of 9α-fluoro-16β-methyl-1,4,6,-pregnatriene-11β,17α,21-triol-3,20-dione 21-acetate (6 gms.) in tetramethylene sulfone (200 ml.) at room temperature add a solution of anhydrous hydrogen fluoride in pyridine (70% v/v, 190 ml.) followed by N-chlorosuccinimide (3.24 gms.). Stir the reaction mixture for 1¼ hours, then pour into aqueous sodium bicarbonate solution and extract with ethyl acetate. Wash the combined ethyl acetate extracts with dilute hydrochloric acid and water and evaporate. Chromatograph the resultant residue over silica gel via a gradient elution utilizing petroleum ether with increasing amounts of ethyl ether. Combine the like fractions containing the desired product as determined by thin layer chromatography, evaporate and crystallize the resultant residue from methylene chloride to obtain 6β,9α-difluoro-7α-chloro-16β-methyl-1,4,-pregnadiene-11β,17α,21-triol-3,20-dione 21-acetate, yield 1.9 gms., m.p. 230°–235° C.; $[\alpha]_D^{26} + 59°$ (chloroform); $\lambda_{max}^{methanol}$ 238 nm ($\epsilon = 15,100$).

B. Treat each of 16α-methyl-1,4,6-pregnatriene-11β,17α,21-triol-3,20-dione 21-acetate and 9α,11β-dichloro-16α-methyl-1, 4,6-pregnatriene-17α,21-diol-3,20-dione 21-acetate with anhydrous hydrogen fluoride and N-chlorosuccinimide in the manner described in Example 1A and isolate and purify each of the resultant products in the described manner to obtain, respectively, 6β-fluoro-7α-chloro-16α-methyl-1,4-pregnadiene-11β,17α,21-triol-3,20-dione 21-acetate, m.p. 230°–233° C., $[\alpha]_D^{26}$ +38° (chloroform), $\lambda_{max}^{methanol}$ 244 nm (ε=14,700); and 6β-fluoro-7α,9α, 11β-trichloro-16α-methyl-1,4-pregnadiene-17α,21-diol-3,20-dione 21-acetate.

EXAMPLE 2

6β,9α-DIFLUORO-7α-BROMO-16-METHYL-1,4-PREGNADIENE-11β,17α,21-TRIOL-3,20-DIONE 21-ACETATES

A. To a solution of 9α-fluoro-16β-methyl-1,4,6-pregnatriene-11β,17α,21-triol-3,20-dione 21-acetate (6 gms.) in tetramethylene sulfone (100 ml.) at room temperature add a solution of anhydrous hydrogen fluoride in pyridine (70% v/v, 95 ml.) followed by N-bromosuccinimide (9.0 gms.). Stir the reaction mixture at room temperature for 20 hours, then pour the reaction mixture into aqueous sodium bicarbonate and extract with ethyl acetate. Wash the combined extracts with dilute hydrochloric acid and then with water, dry over magnesium sulfate and evaporate. Chromatograph the resultant residue over silica gel eluting with chloroform: ethyl acetate (85:15 v/v), combine the like fractions as determined by thin layer chromatography and evaporate to a residue comprising 6β,9α-difluoro-7α-bromo-16β-methyl-1,4-pregnadiene-11β,17α,21-triol-3,20-dione 21-acetate, yield 2.2 gms., m.p. 230° C., $[\alpha]_D^{26}$ +34° (chloroform), $\lambda_{max}^{methanol}$ 239 nm (ε=14,800).

B. Treat 9α-fluoro-16α-methyl-1,4,6-pregnatriene-11β,17α,21-triol-3,20-dione 21-acetate in a manner similar to that described in Example 2A to obtain 6β,9α-difluoro-7α-bromo-16α-methyl-1,4-pregnadiene-11β,17α,21-triol-3,20-dione 21-acetate, m.p. 250°–252° C., $[\alpha]_D^{26}$ +23° (chloroform), $\lambda_{max}^{methanol}$ 238 nm (ε=14,600).

EXAMPLE 3

6β,9α-DIFLUORO-7α-IODO-16-METHYL-1,4-PREGNADIENE-11β,17α,21-TRIOL-3,20-DIONE 21-ACETATES

A. To a stirred solution of anhydrous hydrogen fluoride (7 ml.) in dimethylformamide (10 ml.) at −50° C., add 9α-fluoro-16α-methyl-1,4,6-pregnatriene-11β,17α,21-triol-3,20-dione 21-acetate (864 mg.) and recrystallized N-iodosuccinimide (1.8 gms.). Allow the reaction mixture to warm to room temperature and then continue stirring for 80 minutes. Pour the reaction mixture into aqueous sodium bicarbonate solution, filter the resultant precipitate, wash with water, air dry and then recrystallize from ether/petroleum ether to obtain 6β,9α-difluoro-7α-iodo-16α-methyl-1,4-pregnadiene-11β,17α,21-triol-3,20-dione 21-acetate, yield 330 mg., m.p. 230°–232° C., $[\alpha]_D^{26}$ +19° (chloroform); $\lambda_{max}^{methanol}$ 238 nm (ε=14,500).

B. Treat 9α-fluoro-16β-methyl-1,4,6-pregnatriene-11β,17α,21-triol-3,20-dione 21-acetate with hydrogen fluoride and N-iodo-succinimide in a manner similar to that described in Example 3A to obtain 6β,9α-difluoro-7α-iodo-16β-methyl-1,4-pregnadiene-11β,17α,21-triol-3,20-dione 21-acetate, m.p. 210° C., $\lambda_{max}^{methanol}$ 237 nm (ε=15,000).

EXAMPLE 4

6β,9α-DIFLUORO-7α-HALOGENO-16-METHYL-1,4-PREGNADIENE-11β,17α,21-TRIOL 3,20-DIONES

A. To a solution of 6β,9α-difluoro-7α-chloro-16β-methyl-1,4-pregnadiene-11β,17α,21-triol-3,20-dione 21-acetate (2.2 gms.) in methanol (300 ml.) add a 10% aqueous sodium bicarbonate solution (40 ml.) and stir the reaction mixture under an atmosphere of nitrogen at room temperature for 2 hours. Remove most of the solvent in vacuo, then dilute the resultant residue with water (100 ml.). Separate the resultant precipitate by filtration, wash with water, air dry and recrystallize from acetone/hexane to obtain 6β,9α-difluoro-7α-chloro-16β-methyl-1,4-pregnadiene-11β,17α,21-triol-3,20-dione, yield 1.67 gms., m.p. 213°–217° C., $[\alpha]_D^{26}$ −51° (dioxane), $\lambda_{max}^{methanol}$ 238 nm (ε=15,400).

B. In a manner similar to that described in Example 4A, treat each of 6β,9α-difluoro-7α-bromo-16β-methyl-1,4-pregnadiene-11β,17α,21-triol-3,20-dione 21-acetate, 6β,9α-difluoro-7α-bromo-16α-methyl-1,4-pregnadiene-11β,17α,21-triol-3,20-dione, and 6β,9α-difluoro-7α-iodo-16α-methyl-1,4-pregnadiene-11β,17α,21-triol-3,20-dione 21-acetate with aqueous sodium bicarbonate, then isolation and purification thereof to obtain, respectively, 6β,9α-difluoro-7α-bromo-16β-methyl-1,4-pregnadiene-11β,17α,21-triol-3,20-dione, m.p. 190° C., $[\alpha]_D^{26}$ +43° C. (dioxane), $\lambda_{max}^{methanol}$ 237 nm (ε=15,900); 6β,9α-difluoro-7α-bromo-16α-methyl-1,4-pregnadiene-11β,17α,21-triol-3,20-dione, m.p. 107° C., $\lambda_{max}^{methanol}$ 238 nm (ε=13,600); and 6β,9α-difluoro-7α-iodo-16α-methyl-1,4-pregnadiene-11β,17α,21-triol-3,20-dione, m.p. 190° C., $[\alpha]_D^{26}$ +10° (chloroform), $\lambda_{max}^{methanol}$ 239 nm (ε=14,900).

EXAMPLE 5

6β,9α-DIFLUORO-7α-HALOGENO-16-METHYL-1,4-PREGNADIENE-11β,17α,21-TRIOL-3,20-DIONE 17-LOWERALKANOATES

A. Dissolve 6β,9α-difluoro-7α-chloro-16β-methyl-1,4-pregnadiene-11β,17α,21-triol-3,20-dione (700 mg.) in dimethylsulfoxide (9.0 ml.) containing triethylorthoacetate (1 ml.) and p-toluenesulfonic acid (90 mg.) and stir the reaction mixture at room temperature for 4 hours. Pour the reaction mixture into water and extract with ethyl acetate. Wash the combined ethyl acetate extracts with water, then evaporate to a residue comprising 6β,9α-difluoro-7α-chloro-16β-methyl-1,4-pregnadiene-11β,17α,21-triol-3,20-dione 17,21-ethylorthoacetate. Dissolve the foregoing 17,21-ethylorthoacetate residue in acetic acid (14 ml.) and water (0.2 ml.) and stir overnight at room temperature. Pour the reaction mixture into water, separate the resultant precipitate by filtration, wash with water, air dry and crystallize from acetone/hexane to obtain 6β,9α-difluoro-7α-chloro-16β-methyl-1,4-pregnadiene-11β,17α,21-triol-3,20-dione 17-acetate, yield 450 mg., m.p. 222°–226° C., $[\alpha]_D^{26}$ +26° (dioxane), $\lambda_{max}^{methanol}$ 238 nm (ε=16,000).

B. In similar manner, treat each of 6β,9α-difluoro-7α-iodo-16α-methyl-1,4-pregnadiene-11β,17α,21-triol-3,20-dione and 6β,9α-difluoro-7α-bromo-60methyl-1,4-pregnadiene-11β,17α,21-triol-3,20-dione with triethylorthoacetate followed by reaction of the resulting 17α,21-alkyl ortho esters (i.e., 6β,9α-difluoro-7α-iodo-16α-methyl-1,4-pregnadiene-11β,17α,21-triol-3,20- dione 17,21-ethylorthoacetate and 6β,9α-difluoro-7α-bromo-16α-methyl-1,4-pregnadiene-11β,17α,21-triol-3,20-dione 17,21-ethylorthoacetate) with aqueous acetic acid to obtain, respectively, 6β,9α-difluoro-7α-iodo-16α-methyl-1,4-pregnadiene-11β,17α,21-triol-3,20-dione 17-acetate, m.p. 142° C.; $[\alpha]_D^{26}$ −15° (dioxane); $\lambda_{max}^{methanol}$ 238 nm ($\epsilon$=14,900), and 6β,9α-difluoro-7α-bromo-16α-methyl-1,4-pregnadiene-11β,17α,21-triol-3,20-dione 17-acetate, m.p. 143°-146° C. $[\alpha]_D^{26}$ −45° (chloroform), $\lambda_{max}^{methanol}$ 237 nm ($\epsilon$=16,800).

C. In the procedure of Example 5A, by substituting triethylorthopropionate for triethylorthoacetate, there is obtained 6β,9α-difluoro-7α-chloro-16β-methyl-1,4-pregnadiene-11β,17α,21-triol-3,20-dione 17-propionate, m.p. 224°-227° C., $[\alpha_D^{26}$ +21° (dioxane), $\lambda_{max}^{methanol}$ 238 nm ($\epsilon$=15,300).

In a manner similar to that described hereinabove, treat each of 6β,9α-difluoro-7α-bromo-16β-methyl-1,4-pregnadiene-11β,17α,21-triol-3,20-dione and 6β,9α-difluoro-7α-bromo-16α-methyl-1,4-pregnadiene-11β,17α,21-triol-3,20-dione with triethylorthopropionate and p-toluenesulfonic acid followed by treatment of the resulting 17,21-ethylorthopropionate ester produced thereby with aqueous acetic acid to obtain, respectively, 6β,9α-difluoro-7α-bromo-16β-methyl-1,4-pregnadiene-11β,17α,21-triol-3,20-dione 17-propionate, m.p. 195°-200° C., $[\alpha]_D^{26}$ +24° (dioxane), $\lambda_{max}^{methanol}$ 238 nm ($\epsilon$=15,100), and 6β,9α-difluoro-7α-bromo-16α-methyl-1,4-pregnadiene-11β,17α,21-triol-3,20-dione 17-propionate.

D. In a manner similar to that described in Example 5A, treat 6β,9α-difluoro-7α-bromo-16α-methyl-1,4-pregnadiene-11β,17α,21-triol-3,20-dione with tributylorthovalerate and p-toluenesulfonic acid followed by treatment of the 17,21-butylorthopropionate ester thereby formed with aqueous acetic acid to obtain 6β,9α-difluoro-7α-bromo-16α-methyl-1,4-pregnadiene-11β,17α,21-triol-3,20-dione-17-valerate, m.p. 120° C., $\lambda_{max}^{methanol}$ 237 nm ($\epsilon$=14,000), $[\alpha]_D^{26}$ −33° (chloroform).

EXAMPLE 6

6β-FLUORO-7α-HALOGENO-16-METHYL-1,4-PREGNADIENE-11β,17α,21-TRIOL-3,20-DIONE 17,21-DILOWERALKANOATES

A. To a solution of 6β,9α-difluoro-7α-chloro-16β-methyl-1,4-pregnadiene-11β,17α,21-triol-3,20-dione 17-acetate (180 mg.) in pyridine (0.4 ml.) add acetic anhydride (0.2 ml.) and allow the solution to remain at room temperature overnight. Pour the reaction mixture into dilute hydrochloric acid, separate the resultant precipitate by filtration, wash with water, dry and chromatograph over silica gel via a gradient utilizing petroleum ether with increasing amounts of ethyl ether. Combine the like extracts as determined by thin layer chromatography, evaporate and crystallize the resultant residue from ether/petroleum ether to yield 6β,9α-difluoro-7α-chloro-16β-methyl-1,4-pregnadiene-11β,17α,21-triol-3,20-dione 17,21-diacetate, yield 73 mg., m.p. 142° C., $[\alpha]_D^{26}$ +12° (chloroform).

B. In a manner similar to that described in Example 6A, prepare the following 17,21-diloweralkanoates from the corresponding 17-monoalkanoates of Example 5 with the appropriate acid anhydride: 6β,9α-difluoro-7α-chloro-16β-methyl-1,4-pregnadiene-11β,17α,21-triol-3,20-dione 17-acetate 21-propionate, m.p. 135°-140° C., $[\alpha]_D^{26}$ +16° (chloroform); 6β,9α-difluoro-7α-chloro-16β-methyl-1,4-pregnadiene-11β,17α,21-triol-3,20-dione 17-propionate 21-acetate, m.p. 130°-135° C., $[\alpha]_D^{26}$+19.2° (dioxane), $\lambda_{max}^{methanol}$ 237 nm ($\epsilon$=16,800); 6β,9α-difluoro-7α-chloro-16β-methyl-1,4-pregnadiene-11β,17α,21-triol-3,20-dione-17,21-dipropionate, m.p. 110°-115° C., $[\alpha]_D^{26}$ +18° (dioxane), $\lambda_{max}^{methanol}$ 238 nm ($\epsilon$=15,100); 6β,9α-difluoro-7α-chloro-16β-methyl-1,4-pregnadiene-11β,17α,21-triol-3,20-dione 17-propionate 21-n-butyrate, m.p. 105° C., $[\alpha]_D^{26}$ +21° (chloroform), $\lambda_{max}^{methanol}$ 237 nm ($\epsilon$=15,800); 6β,9α-difluoro-7α-bromo-16β-methyl-1,4-pregnadiene-11β,17α,21-triol-3,20-dione 17-propionate 21-acetate, m.p. 120°-125° C., $[\alpha]_D^{26}$ +18° (dioxane), $\lambda_{max}^{methanol}$ 238 nm ($\epsilon$=14,500); 6β,9α-difluoro-7α-bromo-16β-methyl-1,4-pregnadiene-11β,17α,21-triol-3,20-dione 17,21-dipropionate, m.p. 112° C., $[\alpha]_D^{26}$ +14° (dioxane), $\lambda_{max}^{methanol}$ 238 nm ($\epsilon$=15,100); 6β,9α-difluoro-7α-bromo-16β-methyl-1,4-pregnadiene-11β,17α,21-triol-3,20-dione 17-propionate 21-n-butyrate, m.p. 181°-183° C., $[\alpha]_D^{26}$ +20° (chloroform), $\lambda_{max}^{methanol}$ 239 ($\epsilon$=15,600); 6β,9α-difluoro-7α-bromo-16αmethyl-1,4-pregnadiene-11β,17α,21-triol-3,20-dione 17,21-diacetate, m.p. 97° C., $\lambda_{max}^{methanol}$ 237 nm ($\epsilon$=14,100).

C. To a solution of 16α-methyl-1,4,6-pregnatriene-11β,17α,21-triol-3,20-dione 17,21-dipropionate (207 mg.), in tetramethylene sulfone (7 ml.) at room temperature, add a solution of anhydrous hydrogen fluoride in pyridine (70% v/v, 14 ml.) followed by N-chlorosuccinimide (62 mg.). Stir the reaction mixture at room temperature for 3 hours, and pour into aqueous sodium bicarbonate solution. Separate the resultant precipitate by filtration, wash with water, dry and purify by chromatographing over silica gel eluting with petroleum ether/ether (1:1), combine the like fractions as determined by thin layer chromatography, evaporate and crystallize the resultant residue from ether/petroleum ether to obtain 6β-fluoro-7α-chloro-16α-methyl-1,4-pregnadiene-11β,17α,21-triol-3,20-dione 17,21-dipropionate, yield 97 mg., m.p. 207°-208° C. $[\alpha]_D^{26}$ +11.0° (chloroform), $\lambda_{max}^{methanol}$ 243 nm ($\epsilon$=13,800).

EXAMPLE 7

6β,9α-DIFLUORO-7α-BROMO-16α-METHYL-1,4-PREGNADIENE-11β,17α,21-TRIOL-3,20-DIONE 21-TRIMETHYLACETATE

To a solution of 6β,9α-difluoro-7α-bromo-16α-methyl-1,4-pregnadiene-11β,17α,21-triol-3,20-dione (200 mg.) in pyridine (0.4 ml.) add trimethylacetic anhydride (0.4 ml.) and heat the reaction mixture at 70° C. for 2 days. Cool the reaction mixture, pour into dilute hydrochloric acid and extract with ethyl acetate. Wash the combined ethyl acetate extracts with water, dry over magnesium sulfate, evaporate and chromatograph the resultant residue on silica gel thick layer plates eluting with chloroform/ethyl acetate (3:1). Extract the more polar band with ethyl acetate, evaporate the ethyl acetate extract and recrystallize the resultant residue from ether/isopropylether to obtain 6β,9α-difluoro-7α-bromo-16α-methyl-1,4-pregnadiene-11β,17α,21-triol-3,20-dione 21-trimethylacetate, m.p. 229° C., $\lambda_{max}^{methanol}$ 237 nm ($\epsilon$=15,100).

EXAMPLE 8

6β-FLUORO-7α-CHLORO-1,4-PREGNADIENE-11β,17α,21-TRIOL-3,20-DIONE 21-ACETATE

To a solution of 1,4,6-pregnatriene-11β,17α,21-triol-3,20-dione 21-acetate (1 g., 2.5 mmols) in sulfolane (20 ml.) at room temperature, add pyridine/hydrogen fluoride (20 ml., 70:30 v/v and N-chlorosuccinimide (665 mg., 5.0 mmols) and stir the reaction mixture for 2.5 hours. Pour the reaction mixture into dilute hydrochloric acid and separate the resultant precipitate by filtration, wash the precipitate with water and dry. Purify by recrystallization from ethyl acetate to obtain 6β-fluoro-7α-chloro-1,4-pregnadiene-11β,17α,21-triol-3,20-dione 21-acetate, yield 425 mg., m.p. 275°–280° C.; $[\alpha]_D^{26}$ +72° (dioxane); $\lambda_{max}^{methanol}$ 242 nm (ϵ=14,900).

EXAMPLE 9

6β,7α,9α-TRIFLUORO-16β-METHYL-1,4-PREGNADIENE-11β,17α,21-TRIOL-3,20-DIONE 21-ACETATE

To a solution of 9α-fluoro-16β-methyl-1,4,6-pregnatriene-11β,17α,21-triol-3,20-dione 21-acetate (432 mg., 1.0 mmol) in tetrahydrofuran (30 ml.), add sodium trifluoroacetate (400 mg.) and cool the reaction mixture to −78° C. Bubble into this solution a mixture of fluorine and nitrogen (2.5:97.5 v/v) slowly for 2 hours with stirring. Purge the reaction mixture with nitrogen, allow the reaction mixture to warm to room temperature, and evaporate the solvent and chromatograph the resultant residue over silica gel GF eluting with chloroform in ethyl acetate (3:1). Combine the like fractions containing the desired product as determined by thin layer chromatography and evaporate to a residue comprising 6β,7α,9α-trifluoro-16β-methyl-1,4-pregnadiene-11β,17α,21-triol-3,20-dione 21-acetate, yield 56 mg. Purify further by crystallization from ether/petroleum ether, m.p. 180°–182° C., $[\alpha]_D^{26}$ +66° (chloroform), $\lambda_{max}^{methanol}$ 236 nm (ϵ13,000).

EXAMPLE 10

6β,7α,9α-TRIFLUORO-16β-METHYL-1,4-PREGNADIENE-11β,17α,21-TRIOL-3,20-DIONE 17,21-DIPROPIONATE

To a solution of 9α-fluoro-16β-methyl-1,4,6-pregnatriene-11β,17α,21-triol-3,20-dione 17,21-dipropionate (1 gm.) in chloroform (75 ml.), cool to −78° C., add sodium trifluoroacetate (1 gm.). Bubble into this solution a mixture of fluorine and nitrogen (2.5:97.5 v/v) slowly for 1 hour with stirring. Purge the reaction mixture with nitrogen, allow to warm to room temperature, evaporate to dryness and chromatograph the resultant residue over silica gel GF eluting with chloroform/ethyl acetate (3:1). Combine the like fractions containing the desired product as determined by thin layer chromatography to obtain 6β,7α,9α-trifluoro-16β-methyl-1,4-pregnadiene-11β,17α,21-triol-3,20-dione 17,21-dipropionate, m.p. 118°–122° C., $[\alpha]_D^{26}$ +45 (chloroform). $\lambda_{max}^{methanol}$ 235 nm (ϵ=12,200).

We claim:

1. The method of treating an inflammatory condition in a warm-blooded animal responsive to treatment with anti-inflammatory agents, which comprises applying topically to the inflamed area, a non-toxic, anti-inflammatory-effective amount of a 6β-fluoro-7α-halogeno-1,4-pregnadiene of the following formula I together with a non-toxic, pharmaceutically acceptable carrier:

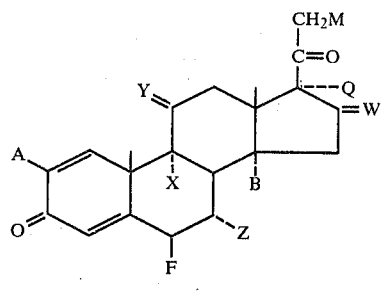

wherein A is hydrogen, or when Y is (H,β—OH), then A is also chlorine, bromine or methyl;

B is hydrogen, or taken together with Q is 14α,17α-alkylidenedioxy;

X is a member selected from the group consisting of hydrogen, fluorine and chlorine;

Y is (H,β—OH), (H,β—OCOH), or when X is chlorine then Y is also (H,β—fluorine) or (H,β-chlorine);

Z is halogen;

Q is OV wherein V is hydrogen or an acyl radical of a hydrocarboncarboxylic acid having up to 8 carbon atoms;

W is a member selected from the group consisting of (H,H), (H, lower alkyl); (H,α-OV₁) wherein V₁ is hydrogen or an acyl radical of an acid selected from the group consisting of a hydrocarboncarboxylic acid having up to 12 carbon atoms and retinoic acid; =CHT wherein T is a member selected from the group consisting of hydrogen, lower alkyl, fluorine and chlorine; and W together with Q is 16α,17α-lower alkylidenedioxy, 16α,17α-cycloalkylidenedioxy or 16α,17α-alkylorthoalkanoate; and M is a member selected from the group consisting of chlorine and fluorine provided Q is other than hydroxy, and OV₂ wherein V₂ is hydrogen or an acyl radical of an acid selected from the group consisting of a hydrocarboncarboxylic acid having up to 12 carbon atoms, a hydrocarbonsulfonic acid having up to 12 carbon atoms; retinoic acid, and phosphoric acid and mono and di-alkali and alkaline earth metal salts thereof; and OV₂ together with OV is a member selected from the group consisting of alkylidenedioxy and alkylorthoalkanoate.

2. The method according to claim 1 wherein X is chlorine or fluorine and W is other than (H,H).

3. The method according to claims 1 or 2 wherein V is an acyl radical of an unsubstituted hydrocarboncarboxylic acid having up to 8 carbon atoms or of benzoic acid substituted by a halogen or a methoxy group.

4. The method according to claims 1 or 2 wherein W is (H, CH₃).

5. The method according to claim 3 wherein W is (H, CH₃).

6. The method according to claim 1 for the topical treatment of an inflammatory condition which comprises applying to the inflamed area in a concentration effective for the topical treatment of inflammation, a 6β-fluoro-7α-halogeno-16-methyl-1,4-pregnadiene of the following formula II:

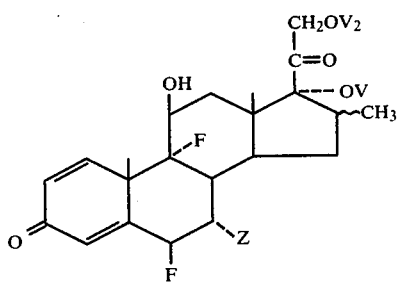

wherein each of V and V₂ are independently hydrogen or an acyl radical of a hydrocarboncarboxylic acid having up to 4 carbon atoms, and Z is halogen.

7. The method of claim 6 when V is an acyl radical of a hydrocarboncarboxylic acid having up to 4 carbon atoms.

8. The method of claims 6 or 7 when Z is chlorine or bromine.

9. The method of claims 6 or 7 when said 16-methyl derivative is a 16β-methyl derivative of formula II wherein Z is chlorine or bromine.

10. The method of claims 6 or 7 when said 16-methyl derivative is a 16β-methyl of formula II wherein Z is chlorine or bromine and V is propionyl.

11. The method of claim 10 when said 16β-methyl derivative is 6β,9α-difluoro-7α-chloro-16β-methyl-1,4-pregnadiene-11β,17α,21-triol-3,20-dione 17,21-dipropionate.

12. The method of claim 10 when said 16β-methyl derivative is 6β,9α-difluoro-7α-bromo-16β-methyl-1,4-pregnadiene-11β,17α,21-triol-3,20-dione 17,21-dipropionate.

13. A topical pharmaceutical composition for use in the topical treatment of inflammation which comprises a topically anti-inflammatory effective amount of 6β-fluoro-7α-halogeno-1,4-pregnadiene of claim 1 together with a non-toxic, pharmaceutically acceptable topical carrier.

14. A topical pharmaceutical composition of claim 13 for use in the topical treatment of inflammation which comprises a topically anti-inflammatory effective amount of a 6β-fluoro-7α-halogeno-16-methyl-1,4-pregnadiene of formula II, claim 6, together with a non-toxic, pharmaceutically acceptable topical carrier.

15. A topical pharmaceutical composition of claim 14 comprising a 6β-fluoro-7α-halogeno-16β-methyl-1,4-pregnadiene of formula II, claim 6, wherein Z is chlorine or bromine and V is an acyl radical of a hydrocarboncarboxylic acid having 3 or 4 carbon atoms.

16. A topical pharmaceutical composition of claim 15 wherein said 6β-fluoro-7α-halogeno-16-methyl-1,4-pregnadiene is 6β,9α-difluoro-7α-chloro-16β-methyl-1,4-pregnadiene-11β,17α,21-triol-3,20-dione 17,21-dipropionate.

17. A topical pharmaceutical composition of claim 15 wherein said 6β-fluoro-7α-halogeno-16-methyl-1,4-pregnadiene- is 6β,9α-difluoro-7α-bromo-16β-methyl-1,4-pregnadiene-11β,17α,21-triol-3,20-dione 17,21-dipropionate.

* * * * *